(12) United States Patent
Brock et al.

(10) Patent No.: US 7,504,060 B2
(45) Date of Patent: Mar. 17, 2009

(54) METHOD AND APPARATUS FOR THE PRODUCTION OF NONWOVEN WEB MATERIALS

(75) Inventors: Thomas William Brock, Woodstock, GA (US); Brian Stephen Forbes, Alpharetta, GA (US); Bryan David Haynes, Advance, NC (US); Douglas Jay Hulslander, Woodstock, GA (US); Matthew Boyd Lake, Cumming, GA (US); Eric Edward Lennon, Roswell, GA (US); Hannong Rhim, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 249 days.

(21) Appl. No.: 10/687,006

(22) Filed: Oct. 16, 2003

(65) Prior Publication Data

US 2005/0082723 A1   Apr. 21, 2005

(51) Int. Cl.
*D01D 5/08* (2006.01)
*D04H 3/02* (2006.01)
*D06M 10/00* (2006.01)
(52) U.S. Cl. ............... 264/465; 264/103; 425/83.1; 425/174.8 E
(58) Field of Classification Search ......... 264/109–128, 264/103, 465; 425/83.1, 174.8 E; 442/327
See application file for complete search history.

(56) References Cited

U.S. PATENT DOCUMENTS

| 705,691 | A | | 7/1902 | Morton |
| 2,810,426 | A | | 10/1957 | Till et al. |
| 2,863,493 | A | * | 12/1958 | Snow et al. ............... 156/62.4 |
| 3,052,009 | A | | 9/1962 | Epstein et al. |
| 3,097,056 | A | | 7/1963 | Rowlinson |
| 3,117,055 | A | | 1/1964 | Guandique et al. |
| 3,163,753 | A | | 12/1964 | Sabato et al. |
| 3,293,718 | A | | 12/1966 | Sheets |

(Continued)

FOREIGN PATENT DOCUMENTS

DE       1635585       3/1972

(Continued)

OTHER PUBLICATIONS

ASTM Designation: D 5035-90, Standard Test Method for Breaking Force and Elongation of Textile Fabrics (Strip Force), May 1990.

(Continued)

*Primary Examiner*—Leo B Tentoni
(74) *Attorney, Agent, or Firm*—Dority & Manning, P.A.

(57) ABSTRACT

The present invention provides a method of making a nonwoven web with desired fiber orientation, the method including the steps of providing a source of fibers, subjecting the fibers to an electrostatic charge, deflecting the fibers with a non-contacting deflecting device, collecting the fibers on a moving forming surface to form the nonwoven web. The invention also provides an apparatus for forming fibrous nonwoven webs, the apparatus comprising a source of fibers, a device for applying an electrostatic charge to the fibers, a non-contacting fiber deflecting device adapted to affect the fibers while the fibers are under the influence of the applied electrostatic charge, and a forming surface for collecting the fibers as a fibrous nonwoven web.

17 Claims, 5 Drawing Sheets

U.S. PATENT DOCUMENTS

| | | |
|---|---|---|
| 3,325,906 A | 6/1967 | Franke |
| 3,338,992 A | 8/1967 | Kinney |
| 3,341,394 A | 9/1967 | Kinney |
| 3,384,944 A | 5/1968 | Medeiros et al. |
| 3,402,227 A | 9/1968 | Knee |
| 3,433,857 A | 3/1969 | Dutton et al. |
| T871,003 I4 | 2/1970 | Debbas |
| 3,563,838 A | 2/1971 | Edwards |
| 3,578,739 A | 5/1971 | George |
| 3,655,305 A | 4/1972 | Baxter et al. |
| 3,689,608 A | 9/1972 | Hollberg et al. |
| 3,692,618 A | 9/1972 | Dorschner et al. |
| 3,698,610 A | 10/1972 | Feltgen et al. |
| 3,711,898 A | 1/1973 | Debbas |
| 3,802,817 A | 4/1974 | Matsuki et al. |
| 3,824,052 A | 7/1974 | Fowler |
| 3,849,241 A | 11/1974 | Butin et al. |
| 3,855,046 A | 12/1974 | Hansen et al. |
| 3,860,369 A | 1/1975 | Brethauer et al. |
| 3,967,118 A | 6/1976 | Sternberg |
| 3,991,244 A | 11/1976 | Debbas |
| 4,009,508 A | 3/1977 | Sternberg |
| 4,041,203 A | 8/1977 | Brock et al. |
| 4,163,305 A | 8/1979 | Semjonow et al. |
| 4,208,366 A | 6/1980 | Kinney |
| 4,233,014 A | 11/1980 | Kinney |
| 4,340,563 A | 7/1982 | Appel et al. |
| 4,380,104 A | 4/1983 | Kamioka et al. |
| 4,405,297 A | 9/1983 | Appel et al. |
| 4,430,277 A | 2/1984 | Lin |
| 4,486,365 A | 12/1984 | Kliemann et al. |
| 5,108,820 A | 4/1992 | Kaneko et al. |
| 5,108,827 A | 4/1992 | Gessner |
| 5,122,048 A | 6/1992 | Deeds |
| 5,187,005 A | 2/1993 | Stahle et al. |
| 5,225,018 A | 7/1993 | Zeldin et al. |
| 5,227,172 A | 7/1993 | Deeds |
| 5,244,724 A * | 9/1993 | Antonacci et al. ............ 442/414 |
| 5,336,552 A | 8/1994 | Strack et al. |
| 5,382,400 A | 1/1995 | Pike et al. |
| 5,397,413 A | 3/1995 | Trimble et al. |
| 5,399,423 A | 3/1995 | McCullough et al. |
| 5,407,739 A | 4/1995 | McCullough et al. |
| 5,707,468 A | 1/1998 | Arnold et al. |
| 5,762,857 A * | 6/1998 | Weng et al. .................. 264/465 |
| 5,807,795 A | 9/1998 | Lau et al. |
| 5,970,583 A | 10/1999 | Groten et al. |
| 5,989,004 A | 11/1999 | Cook |
| 6,365,088 B1 | 4/2002 | Knight et al. |
| 6,386,260 B1 | 5/2002 | Ferencz et al. |
| 6,709,623 B2 * | 3/2004 | Haynes et al. ............... 264/465 |
| 6,797,101 B2 * | 9/2004 | Ferencz et al. ............... 156/167 |
| 6,989,125 B2 * | 1/2006 | Boney et al. ................. 264/465 |
| 2002/0117770 A1 | 8/2002 | Haynes et al. |

FOREIGN PATENT DOCUMENTS

| | | |
|---|---|---|
| EP | 0 950 744 A1 | 10/1999 |
| EP | 1 217 107 A1 | 6/2002 |
| GB | 1244753 | 9/1971 |
| WO | WO 02/34990 | 5/2002 |
| WO | WO 02/34991 | 5/2002 |
| WO | WO 02/052071 | 7/2002 |
| WO | WO 02/052072 | 7/2002 |
| WO | WO 03/038174 | 5/2003 |

OTHER PUBLICATIONS

Abstract, JP 03173911B2, Jun. 4, 2001, Nagaoka et al.
Abstract, JP 10251959A, Sep. 22, 1998, Shimizu.
Abstract, JP 10292256A, Nov. 4, 1998, Hikasa et al.
Abstract, JP 11131355A, May 18, 1999, Hikasa et al.

* cited by examiner

METHOD AND APPARATUS FOR THE PRODUCTION OF NONWOVEN WEB MATERIALS

FIELD

The present invention is related to a method for forming nonwoven webs, and to an apparatus for forming such webs.

BACKGROUND OF THE INVENTION

Many of the medical care garments and products, protective wear garments, mortuary and veterinary products, and personal care products in use today are partially or wholly constructed of nonwoven web materials. Examples of such products include, but are not limited to, consumer and professional medical and health care products such as surgical drapes, gowns and bandages, protective workwear garments such as coveralls and lab coats, and infant, child and adult personal care absorbent products such as diapers, training pants, swimwear, incontinence garments and pads, sanitary napkins, wipes and the like. For these applications nonwoven fibrous webs provide tactile, comfort and aesthetic properties which can approach those of traditional woven or knitted cloth materials. Nonwoven web materials are also widely utilized as filtration media for both liquid and gas or air filtration applications since they can be formed into a filter mesh of fine fibers having a low average pore size suitable for trapping particulate matter while still having a low pressure drop across the mesh.

Nonwoven web materials have a physical structure of individual fibers or filaments which are interlaid in a generally random manner rather than in a regular, identifiable manner as in knitted or woven fabrics. The fibers may be continuous or discontinuous, and are frequently produced from thermoplastic polymer or copolymer resins from the general classes of polyolefins, polyesters and polyamides, as well as numerous other polymers. Blends of polymers or conjugate multicomponent fibers may also be employed. Nonwoven fibrous webs formed by melt extrusion processes such as spunbonding and meltblowing, as well as those formed by dry-laying processes such as carding or air-laying of staple fibers are well known in the art. In addition, nonwoven fabrics may be used in composite materials in conjunction with other nonwoven layers as in a spunbond/meltblown (SM) and spunbond/meltblown/spunbond (SMS) laminate fabrics, and may also be used in combination with thermoplastic films. Nonwoven fabrics may also be bonded, embossed, treated and/or colored to impart various desired properties, depending on end-use application.

Melt extrusion processes for spinning continuous filament yarns and continuous filaments or fibers such as spunbond fibers, and for spinning microfibers such as meltblown fibers, and the associated processes for forming nonwoven webs or fabrics therefrom, are well known in the art. Typically, fibrous nonwoven webs such as spunbond nonwoven webs are formed with the fiber extrusion apparatus, such as a spinneret, and fiber attenuating apparatus, such as a fiber drawing unit (FDU), oriented in the cross-machine direction or "CD". That is, the apparatus is oriented at a 90 degree angle to the direction of web production. The direction of nonwoven web production is known as the "machine direction" or "MD". Although the fibers are laid on the forming surface in a generally random manner, still, because the fibers generally exit the CD oriented spinneret and FDU in a direction substantially parallel to the MD, the resulting nonwoven webs have an overall average fiber directionality wherein more of the fibers are oriented in the MD than in the CD. It is widely recognized that such properties as material tensile strength, extensibility and material barrier, for example, are a function of the material uniformity and the directionality of the fibers or filaments in the web. Various attempts have been made to distribute the fibers or filaments within the web in a controlled manner, attempts including the use of electrostatics to impart a charge to the fibers or filaments, the use of spreader devices to direct the fibers or filaments in a desired orientation, the use of mechanical deflection means for the same purpose, and reorienting the fiber forming means. However, it remains desired to achieve still further capability to gain this control in a way that is consistent with costs dictated by the disposable applications for many of these nonwovens.

SUMMARY OF THE INVENTION

The present invention provides a method of making a nonwoven web with desired fiber orientation, the method including the steps of providing a source of fibers, subjecting the fibers to an electrostatic charge, deflecting the fibers with a non-contacting deflecting device, collecting the fibers on a moving forming surface to form the nonwoven web. In embodiments, the fibers may be substantially continuous fibers provided by melt spinning, and the fibers may be subjected to pneumatic drawing forces prior to being subjected to the electrostatic charge. In certain embodiments, the non-contacting deflecting device may be an air knife which delivers a curtain of air. In other embodiments, the non-contacting deflecting device may be an air jet deflector providing discrete jets of air, and the jets of air may be perturbed, and further the air jets may be angled with respect to the machine direction at an angle of about 15 degrees to about 60 degrees, and/or angled with respect to the horizontal plane at an angle up to about 60 degrees. The electrostatic charge may be provided using a charged pin array. In certain embodiments, the air jet deflector is a target electrode for the charged pin array. The invention further provides nonwoven webs produced in accordance with embodiments of the method.

The invention further provides an apparatus for forming fibrous nonwoven webs, the apparatus comprising a source of fibers, a device for applying an electrostatic charge to the fibers, a non-contacting fiber deflecting device adapted to affect the fibers while the fibers are under the influence of the applied electrostatic charge, and a forming surface for collecting the fibers as a fibrous nonwoven web. In certain embodiments, the source of fibers may be a melt spinning device for producing continuous fibers, the device for applying the electrostatic charge may be a charged pin array, and the apparatus further includes a fiber drawing unit applying pneumatic drawing forces to the continuous fibers. In embodiments, the device for applying the electrostatic charge to the fibers may be located so as to apply the electrostatic charge before the fibers enter the fiber drawing unit, or may be located so as to apply the electrostatic charge to the fibers while the fibers are in the fiber drawing unit, or may be located so as to apply the electrostatic charge to the fibers after the fibers exit the fiber drawing unit and before the fibers are collected on the forming surface. In embodiments, the non-contacting fiber deflecting device may be an air jet deflector providing discrete jets of air which are substantially constant or are perturbed. The air jet deflector may be a target electrode for the device for applying electrostatic charge. The air jets may be oriented at an angle with respect to the machine direction or the horizontal plane, or both, the angle determined by the desired orientation of the fibers in the nonwoven web. The apparatus may further comprise a second air jet deflector located on the opposite side of the fibers from a first air jet deflector. Where the device for applying electrostatic charge is a charged pin array, the charged pin array may be located upon a non-contacting deflection device.

DEFINITIONS

Figure 1:
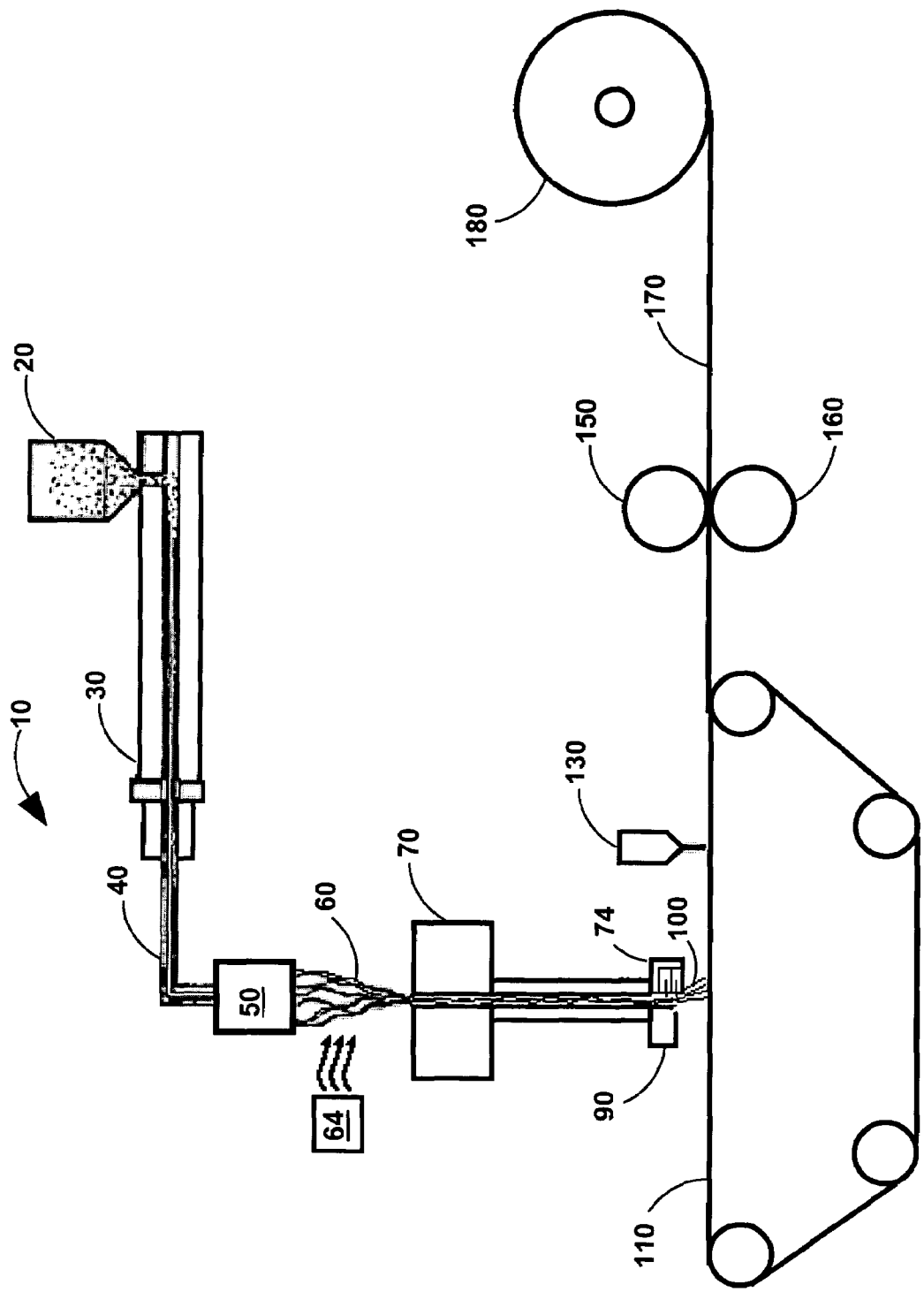
FIG. 1 is a schematic illustration of an exemplary process for producing nonwoven webs.

As used herein and in the claims, the term "comprising" is inclusive or open-ended and does not exclude additional unrecited elements, compositional components, or method steps.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and random symmetries.

As used herein the term "fibers" refers to both staple length fibers and continuous fibers, unless otherwise indicated.

As used herein the term "monocomponent" fiber refers to a fiber formed from one or more extruders using only one polymer. This is not meant to exclude fibers formed from one polymer to which small amounts of additives have been added for color, anti-static properties, lubrication, hydrophilicity, etc. These additives, e.g. titanium dioxide for color, are generally present in an amount less than 5 weight percent and more typically about 2 weight percent.

As used herein the term "multicomponent fibers" refers to fibers which have been formed from at least two component polymers, or the same polymer with different properties or additives, extruded from separate extruders but spun together to form one fiber. Multicomponent fibers are also sometimes referred to as conjugate fibers or bicomponent fibers. The polymers are arranged in substantially constantly positioned distinct zones across the cross-section of the multicomponent fibers and extend continuously along the length of the multicomponent fibers. The configuration of such a multicomponent fiber may be, for example, a sheath/core arrangement wherein one polymer is surrounded by another, or may be a side by side arrangement, an "islands-in-the-sea" arrangement, or arranged as pie-wedge shapes or as stripes on a round, oval, or rectangular cross-section fiber. Multicomponent fibers are taught in, for example, U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

As used herein the term "biconstituent fiber" or "multiconstituent fiber" refers to a fiber formed from at least two polymers, or the same polymer with different properties or additives, extruded from the same extruder as a blend and wherein the polymers are not arranged in substantially constantly positioned distinct zones across the cross-section of the multicomponent fibers. Fibers of this general type are discussed in, for example, U.S. Pat. No. 5,108,827 to Gessner.

As used herein the term "nonwoven web" or "nonwoven material" means a web having a structure of individual fibers or filaments which are interlaid, but not in an identifiable manner as in a knitted or woven fabric. Nonwoven webs have been formed from many processes such as for example, meltblowing processes, spunbonding processes, air-laying processes and carded web processes. The basis weight of nonwoven fabrics is usually expressed in grams per square meter (gsm) or ounces of material per square yard (osy) and the fiber diameters useful are usually expressed in microns. (Note that to convert from osy to gsm, multiply osy by 33.91).

The term "spunbond" or "spunbond nonwoven web" refers to a nonwoven fiber or filament material of small diameter fibers that are formed by extruding molten thermoplastic polymer as fibers from a plurality of capillaries of a spinneret. The extruded fibers are cooled while being drawn by an eductive or other well known drawing mechanism. The drawn fibers are deposited or laid onto a forming surface in a generally random manner to form a loosely entangled fiber web, and then the laid fiber web is subjected to a bonding process to impart physical integrity and dimensional stability. The production of spunbond fabrics is disclosed, for example, in U.S. Pat. Nos. 4,340,563 to Appel et al., U.S. Pat. No. 3,692,618 to Dorschner et al., and U.S. Pat. No. 3,802,817 to Matsuki et al. Typically, spunbond fibers or filaments have a weight-per-unit-length in excess of about 1 denier and up to about 6 denier or higher, although both finer and heavier spunbond fibers can be produced. In terms of fiber diameter, spunbond fibers generally have an average diameter of larger than 7 microns, and more particularly between about 10 and about 25 microns, and up to about 30 microns or more.

As used herein the term "meltblown fibers" means fibers or microfibers formed by extruding a molten thermoplastic material through a plurality of fine, usually circular, die capillaries as molten threads or fibers into converging high velocity gas (e.g. air) streams which attenuate the fibers of molten thermoplastic material to reduce their diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Buntin. Meltblown fibers may be continuous or discontinuous, are generally smaller than 10 microns in average diameter and are often smaller than 7 or even 5 microns in average diameter, and are generally tacky when deposited onto a collecting surface.

As used herein, "thermal point bonding" involves passing a fabric or web of fibers or other sheet layer material to be bonded between a heated calender roll and an anvil roll. The calender roll is usually, though not always, patterned on its surface in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Other common patterns include a diamond pattern with repeating and slightly offset diamonds and a wire weave pattern looking as the name suggests, e.g. like a window screen. Typically, the percent bonding area varies from around 10% to around 30% of the area of the fabric laminate web. Thermal point bonding imparts integrity to individual layers by bonding fibers within the layer and/or for laminates of multiple layers, point bonding holds the layers together to form a cohesive laminate.

DETAILED DESCRIPTION OF THE INVENTION

The present invention provides a method for forming continuous fiber nonwoven webs of high uniformity, the method including providing a source of fibers, subjecting the fibers to electrostatic charge, deflecting the fibers with a non-contacting deflecting device and collecting the fibers on a moving forming surface to form a nonwoven web. The present invention further provides an apparatus for forming such nonwoven webs.

The invention will be more fully described with reference to the Figures. Turning to FIG. 1, there is illustrated in schematic form in side view an exemplary process for production of a nonwoven web material. In reference to FIG. 1, the process line 10 is described with reference to production of monocomponent continuous fibers, but it should be understood that the present invention also encompasses nonwoven webs made with multicomponent fibers (that is, fibers having two or more components).

The process line 10 includes an extruder 30 for melting and extruding polymer fed into the extruder 30 from polymer hopper 20. The polymer is fed from extruder 30 through polymer conduit 40 to a spinneret 50. Spinneret 50 forms fibers 60 which may be monocomponent or multicomponent fibers. Where multicomponent fibers are desired, a second extruder fed from a second polymer hopper would be used. Spinnerets for extruding multicomponent continuous fibers are well known to those of ordinary skill in the art and thus are not described here in detail; however, an exemplary spin pack for producing multicomponent fibers is described in U.S. Pat. No. 5,989,004 to Cook, the entire contents of which are herein incorporated by reference.

Polymers suitable for the present invention include the known polymers suitable for production of nonwoven webs and materials such as for example polyolefins, polyesters, polyamides, polycarbonates and copolymers and blends thereof. Suitable polyolefins include polyethylene, e.g., high density polyethylene, medium density polyethylene, low density polyethylene and linear low density polyethylene; polypropylene, e.g., isotactic polypropylene, syndiotactic polypropylene, blends of isotactic polypropylene and atactic polypropylene; polybutylene, e.g., poly(1-butene) and poly(2-butene); polypentene, e.g., poly(1-pentene) and poly(2-pentene); poly(3-methyl-1-pentene); poly(4-methyl-1-pentene); and copolymers and blends thereof. Suitable copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, and the like, as well as blends and copolymers thereof. Suitable polyesters include poly lactide and poly lactic acid polymers as well as polyethylene terephthalate, poly-butylene terephthalate, polytetramethylene terephthalate, polycyclohexylene-1,4-dimethylene terephthalate, and isophthalate copolymers thereof, as well as blends thereof.

The spinneret 50 has openings arranged in one or more rows. The spinneret openings form a downwardly extending curtain of fibers 60 when polymer is extruded through the spinneret. The exemplary process line 10 in FIG. 1 also includes a quench blower 64 positioned adjacent the curtain of fibers 60 extending from the spinneret 50. Air from the quench air blower 64 quenches the fibers 60 extending from the spinneret 50. The quench air can be directed from one side of the fiber curtain as shown in FIG. 1, or both sides of the fiber curtain. As used herein, the term "quench" simply means reducing the temperature of the fibers using a medium that is cooler than the fibers such as using, for example, chilled air streams, ambient temperature air streams, or slightly to moderately heated air streams. The process may desirably further comprise a means (not shown) to carry away fumes produced from the molten polymer such as a vacuum duct mounted above or otherwise near spinneret 50.

A fiber drawing unit or aspirator 70 to receive the quenched fibers is positioned below the spinneret 50 and the quench blower 64. Fiber drawing units or aspirators for use in melt spinning polymers are well known in the art. Suitable fiber drawing units for use in the method of the present invention include, for example, linear fiber aspirators of the types shown in U.S. Pat. No. 3,802,817 to Matsuki et al. and U.S. Pat. Nos. 4,340,563 and 4,405,297 to Appel et al., all herein incorporated by reference.

Generally described, the fiber drawing unit 70 includes an elongate vertical passage through which the fibers are drawn by aspirating air entering from the sides of the passage and flowing downwardly through the passage. Aspirating air is supplied by a blower (not shown). The aspirating air may be heated or unheated. The aspirating air applies pneumatic drawing forces on the fibers and pulls the fibers through the passage of the fiber drawing unit 70 and by the application of drawing forces attenuates the fibers, that is, reduces the diameter of the fibers. Where multicomponent fibers in a crimpable configuration are used and it is desired to activate latent helical crimp in the fibers prior to fiber laydown, the blower supplies heated aspirating air to the fiber drawing unit 70. In this respect, the heated aspirating air both attenuates the fibers and activates the latent helical crimp, as is described in U.S. Pat. No. 5,382,400 to Pike et al. When it is desired to activate the latent helical crimp in the fibers at some point following fiber laydown the blower supplies unheated aspirating air to fiber drawing unit 70. In this instance, heat to activate the latent crimp may be supplied to the web at some point after fiber laydown.

Figure 2:
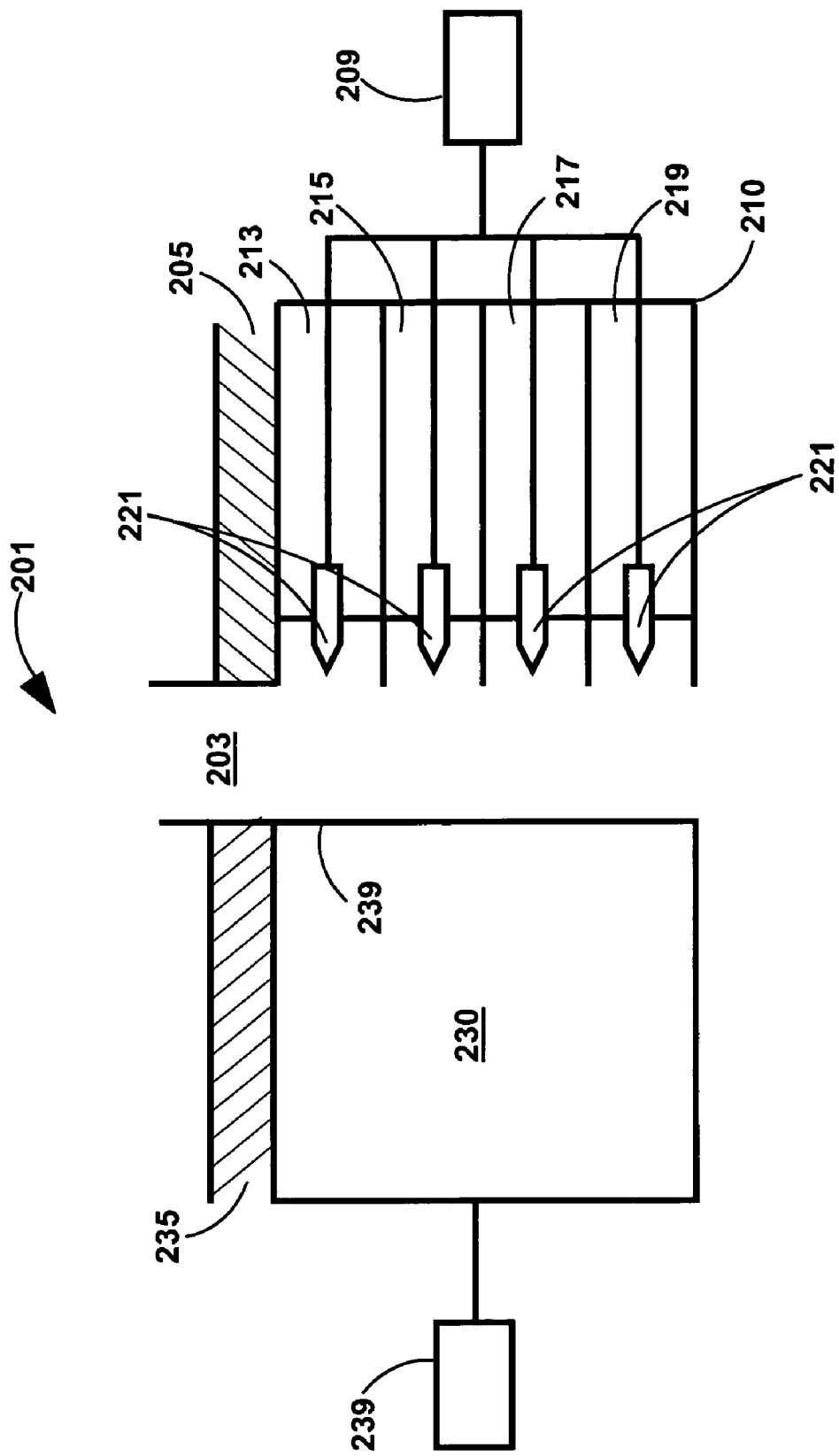
FIG. 2 illustrates an exemplary device for applying electrostatic charge to fibers.

Shown at the exit of fiber drawing unit 70 are non-contacting deflector 90 and electrostatic charging device 74. Electrostatic charging device 74 is a device such as an electrically charged pin array for applying an electrostatic charge to the fibers as they pass out of the elongate vertical passage of the fiber drawing unit and before the fibers are collected upon a forming surface such as the foraminous forming surface 110 shown in FIG. 1. Electrostatic charging devices are known in the art. Generally described, an electrostatic charging device consists of one or more rows of electric emitter pins which produce a corona discharge, thereby imparting an electrostatic charge to the fibers, and the fibers, once charged, will tend to repel one another and help prevent groups of individual fibers from clumping or "roping" together. An exemplary process for charging fibers to produce nonwovens with improved fiber distribution is disclosed in co-assigned PCT Pub. No. WO 02/52071 to Haynes et al. published Jul. 4, 2002, the disclosure of which is incorporated herein by reference. An exemplary electrostatic charging device is shown in FIG. 2. It should be noted that while in FIG. 1 electrostatic charging device 74 is shown positioned below the fiber drawing unit 70, in certain embodiments the charging device 74 may desirably be located above fiber drawing unit 70 to apply the charge to the fibers prior to their entry into drawing unit 70, and in other embodiments the charging device 74 may desirably be located within fiber drawing unit 70 to apply the charge to the fibers as they pass through fiber drawing unit 70.

Turning to FIG. 2, there is shown a side view of one corona discharge arrangement generally designated 201 useful in accordance with the invention. The corona discharge arrangement 201 comprises an electrostatic charging device such as electrode array 210 and a target electrode 230. The exit from fiber drawing unit 70 (FIG. 1) is indicated at 203. Electrode array 210 is connected to power supply 209 and is separated by insulation 205 from the fiber drawing unit. Target electrode 230 may be grounded or connected to power supply 239 and is separated by insulation 235 from the fiber drawing unit. Electrode array 210 comprises multiple bars extending substantially along the cross-machine width of the fiber drawing unit, for example four bars 213, 215, 217 and 219, each of which contains a plurality of emitter pins 221 also extending substantially along the cross-machine width of the fiber drawing unit. Emitter pins are desirably recessed to avoid catching of or fouling with fibers. Target electrode 230 further comprises target plate 231. Returning to FIG. 1, located at the exit of the fiber drawing unit 70 is a non-contacting deflector 90. Non-contacting deflector 90 may be mounted onto the fiber drawing unit 70, or be hung below fiber drawing unit 70 or may be mounted to some other portion of the process equipment without being physically mounted to the fiber drawing unit, and the non-contacting deflector 90 will generally run substantially the entire cross-machine direction length of fiber drawing unit 70. In the case of the process shown in FIG. 1, the non-contacting deflector 90 is also acting as a target electrode for electrostatic charging device 74. By "non-contacting" what is meant is the fibers are deflected to some degree from their travel path prior to fiber laydown, without using a physical object intruding into the fiber flow path or touching the fibers. As an example, the fibers may be deflected by constant or perturbed fluid jets, such as air jets, or by a sheet or curtain of air such as may be produced by using an air knife. Non-contacting deflector 90 may desirably be an air jet deflector such as is shown in FIG. 3.

Figure 3:
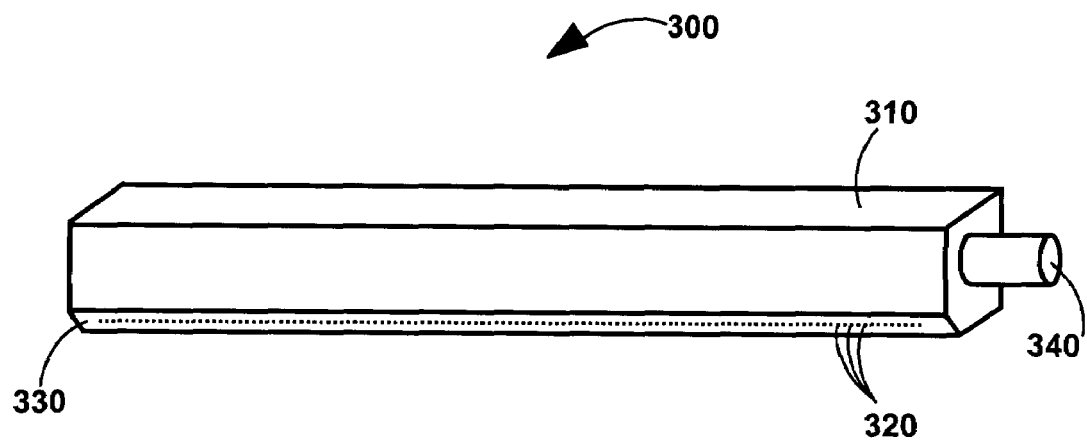
FIG. 3 shows an exemplary non-contacting deflection device.

The air jet deflector, shown generally designated 300 in FIG. 3, comprises a plenum 310 for containing pressurized air and having jet holes 320 which have been bored or drilled or otherwise formed in spaced-apart locations across and through a surface 330 of plenum 310. When air is supplied to plenum 310 through port 340, the jet holes 320 form discrete jets of air. By "discrete" jets of air it is meant that the air initially exits plenum 310 as a plurality of substantially columnar streams of air issuing from jet holes 320 rather than as sheet or curtain of air. It should be noted that although it is said the air initially exits plenum 310 as discrete jets of air, this is not intended to exclude the possibility that at some distance away from the plenum the air jets begin to expand and therefore at some further distance away from plenum 310 the jets may join together. The airjets will be oriented along a direction determined by the angle of orientation of the jet holes 320. The shape, size, spacing and orientation angle of the bored jet holes 320 may be varied to produce intended degrees of fiber separation and desired fiber orientation on fiber laydown.

In certain embodiments, the desired fiber orientation may be achieved by having the jet holes 320 (FIG. 3) oriented to produce air jets which are directed substantially perpendicular to the flow path of the fiber stream exiting the fiber drawing unit 70 (FIG. 1). Generally speaking, the fiber stream will be traveling in a vertical path toward the foraminous forming surface, so where the air jets are directed substantially perpendicular to the flow path of the fiber stream the air jets will be directed substantially in the machine direction and substantially parallel to the horizontal plane. However, depending on desired fiber orientation, it may also be desirable to have the air jets directed at an angle with respect to the machine direction. For example, the air jets may be directed at an angle with respect to the machine direction of up to about 60 degrees, or more. Furthermore, it may be desirable to have the air jets directed at an angle with respect to the horizontal plane, that is, the air jets may be oriented at an upward or downward angle of up to about 60 degrees.

Figure 4A:
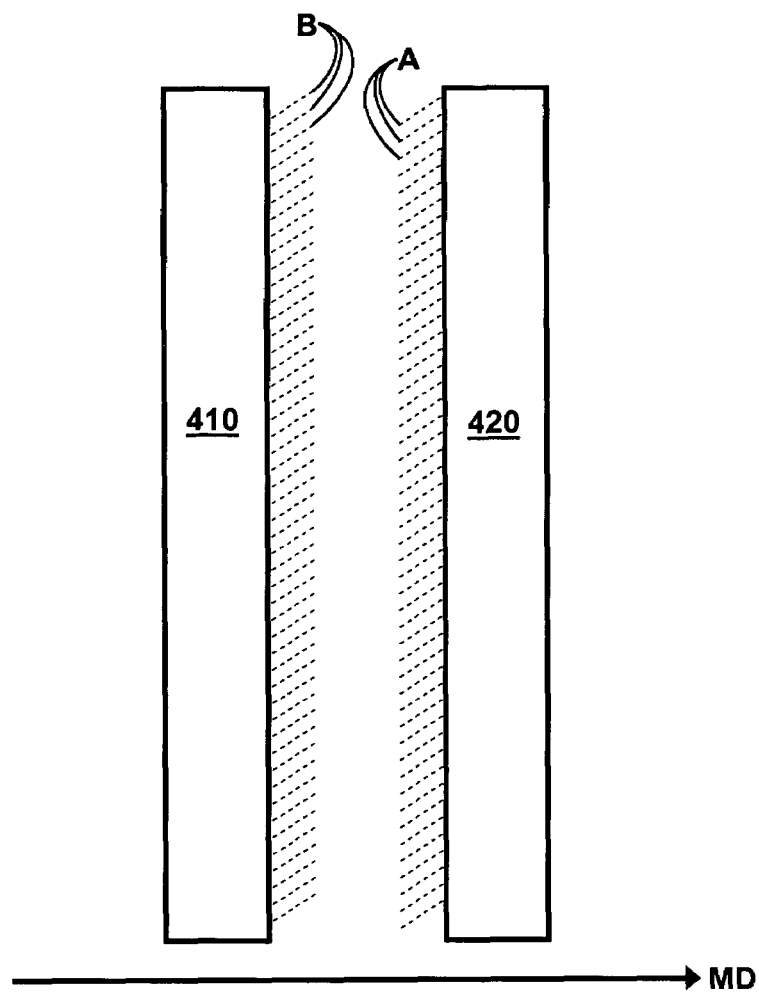
FIG. 4A shows a schematic top view illustration of air flow paths for an opposed pair of exemplary non-contacting deflection devices.
Figure 4B:
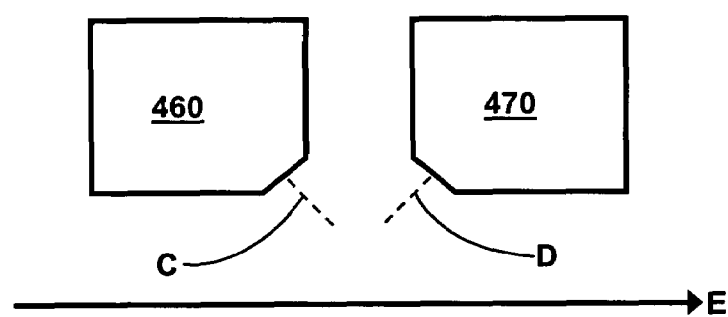
FIG. 4B shows a schematic side view illustration of air flow paths for an opposed pair of exemplary non-contacting deflection devices.

In certain embodiments combinations of angles may also be desirable, such as where the air jets are directed at an angle with respect to the machine direction and also directed at an angle with respect to the horizontal plane. Furthermore, although not shown in the process of FIG. 1, it is desirable to employ more than one non-contacting deflector, that is, to use two non-contacting deflectors as opposed pairs as is illustrated in FIG. 4A and FIG. 4B. In FIG. 4A, a pair of non-contacting deflectors, in this case paired air jet deflectors 410 and 420, are shown in top view. The air jet deflectors 410 and 420 are similar to the air jet deflector which was depicted in FIG. 3 and are punctuated by a series of jet holes (FIG. 3) which are drilled or otherwise formed in the air plenums. The dashed lines A and B illustrate the air jet flow paths during operation of the air jet deflectors. As shown in FIG. 4A, the air jet flow paths are oriented at about a 45 degree angle with respect to arrow MD which represents the machine direction (direction of material production). A side view of a pair of air jet deflectors is shown in FIG. 4B. For the embodiment shown in FIG. 4B, the air jet flow paths during operation of the air jet deflectors are oriented at about a 45 degree downward angle with respect to the horizontal plane (arrow E). The air jet flow paths are illustrated by dashed lines C and D, respectively, for air jet deflectors 460 and 470.

Where an air curtain, such as may be delivered using an air knife, is used to produce the non-contacting deflection (instead of using discrete jets of air) it should be noted that the air curtain may be delivered at an angle substantially perpendicular to the flow path of the fiber stream, or may be delivered at an angle with respect to the horizontal plane as was described above regarding the orientation of air jets. As mentioned above, the fluid or air jets or air curtain may be substantially constant in terms of air velocity and air flow rate, or may alternatively be delivered as a perturbed stream of air. An exemplary method and apparatus for providing perturbation to fluid streams is described in U.S. Pat. No. 5,807,795 to Lau et al., incorporated herein by reference. Perturbation of the fluid streams may be desirable to increase both the degree and order of turbulence of the air flow in the vicinity of the fiber drawing unit exit, thereby increasing the mixing and randomization of the fibers prior to fiber laydown.

Returning to FIG. 1, also shown is endless foraminous forming surface 110 which is positioned below the fiber drawing unit 70 to receive the attenuated fibers 100 from the outlet opening of the fiber drawing unit 70. A vacuum source (not shown) positioned below the foraminous forming surface 110 may be beneficially employed to pull the attenuated fibers onto foraminous forming surface 110. The fibers received onto foraminous forming surface 110 comprise a nonwoven web of loose continuous fibers which may desirably be initially consolidated using consolidation means 130 to assist in transferring the web to a bonding device. Consolidation means 130 may be a mechanical compaction roll as is known in the art, or may be an air knife blowing heated air onto and through the web as is described in U.S. Pat. No. 5,707,468 to Arnold, et al., incorporated herein by reference.

The process line 10 further includes a bonding device such as the calender rolls 150 and 160 shown in FIG. 1 which may be used to thermally point-bond or spot-bond the nonwoven web as described above. Alternatively, where the fibers are multicomponent fibers having component polymers with differing melting points, through-air bonders such as are well known to those skilled in the art may be advantageously utilized. Generally speaking, a through-air bonder directs a stream of heated air through the web of continuous multicomponent fibers thereby forming inter-fiber bonds by desirably utilizing heated air having a temperature at or above the polymer melting temperature of the lower melting polymer component and below the melting temperature of higher melting polymer component. As still other alternatives, the web may be bonded by utilizing other means as are known in the art such as for example adhesive bonding means, ultrasonic bonding means, or entanglement means such as hydroentangling or needling.

Lastly, the process line 10 further includes a winding roll 180 for taking up the bonded web 170. While not shown here, various additional potential processing and/or finishing steps known in the art such as web slitting, stretching, treating, or lamination of the nonwoven fabric into a composite with other materials, such as films or other nonwoven layers, may be performed without departing from the spirit and scope of the invention. Examples of web treatments include electret treatment to induce a permanent electrostatic charge in the web, or in the alternative antistatic treatments. Another example of web treatment includes treatment to impart wettability or hydrophilicity to a web comprising hydrophobic thermoplastic material. Wettability treatment additives may be incorporated into the polymer melt as an internal treatment, or may be added topically at some point following fiber or web formation. Still another example of web treatment includes treatment to impart repellency to low surface energy liquids such as alcohols, aldehydes and ketones. Examples of such liquid repellency treatments include fluorocarbon compounds added to the web or fibers of the web either topically or by adding the fluorocarbon compounds internally to the thermoplastic melt from which the fibers are extruded. In addition, as an alternative to taking the nonwoven web up on winding roll 180, the nonwoven web may be directed to various converting or product forming operations without winding.

As another embodiment of the present invention, the nonwoven web materials may be used in a laminate that contains at least one layer of nonwoven web and at least one additional layer such as a woven fabric layer, an additional nonwoven fabric layer, a foam layer or film layer. The additional layer or layers for the laminate may be selected to impart additional and/or complementary properties, such as liquid and/or microbe barrier properties. The laminate structures, consequently, are highly suitable for various uses including various skin-contacting applications, such as protective garments, covers for diapers, adult care products, training pants and sanitary napkins, various drapes, surgical gowns, and the like. The layers of the laminate can be bonded to form a unitary structure by a bonding process known in the art to be suitable for laminate structures, such as a thermal, ultrasonic or adhesive bonding process or mechanical or hydraulic entanglement processes.

As an example, a breathable film can be laminated to the nonwoven web to provide a breathable barrier laminate that exhibits a desirable combination of useful properties, such as soft texture, strength and barrier properties. As another example the nonwoven web can be laminated to a non-breathable film to provide a strong, high barrier laminate having a cloth-like texture. These laminate structures provide desirable cloth-like textural properties, improved strength properties and high barrier properties. Another laminate structure highly suitable for the present invention is the spunbond-meltblown-spunbond laminate material such as is disclosed in U.S. Pat. No. 4,041,203 to Brock et al., which is herein incorporated in its entirety by reference.

The nonwoven web materials made by the present invention are highly suitable for various uses, such as for example uses including disposable articles, e.g., protective garments, sterilization wraps, surgical garments, wiper cloths, and liners and covers for absorbent articles.

The following examples are provided for illustration purposes and the invention is not limited thereto.

EXAMPLE

Commercially available isotactic polypropylene of approximately 35 melt flow rate, available from ExxonMobil Chemical Co. (Houston, Tex.) and designated as Exxon 3155 was processed in a spun bond type slot-draw nonwoven spinning system to produce Example and Comparative spunbond materials. For all materials, the slot draw process conditions were set to a filament draw speed of about 2700 meters per minute, resulting in an average filament diameter of about 18 microns. For the Example material, an electrostatic charging system was located near the drawing zone exit to charge the filament curtain as generally described in PCT Publication WO 02/52071 to Haynes et al. A two plenum air jet deflection system, each plenum containing a plurality of orifices, was positioned immediately below the charging system and with one plenum on each side of the slot of the slot draw unit. The air jet orifices were oriented at an angle which was 30 degrees downward (from horizontal) and 45 degrees sideward from the machine direction. Air was supplied to each air jet deflector plenum at a pressure of about 17 kPa to produce the air jets, which altered the lay down of the polymer filaments. The filaments were deposited on a foraminous forming surface as a fibrous web material having a basis weight of about 15 grams per square meter. The web was then pattern bonded with a thermal bonding calender, and collected on a winder.

The Example spunbond materials manufactured above were compared with Comparative spunbond materials produced using either air deflection alone or electrostatics with angled tooth mechanical deflection as is described PCT Publication WO 02/52071 to Haynes et al. Material strength and quality of material uniformity of the Example material was measured by the use of a basis weight uniformity test as described below and machine direction (MD) and cross machine direction (CD) tensile test.

Figure 5:
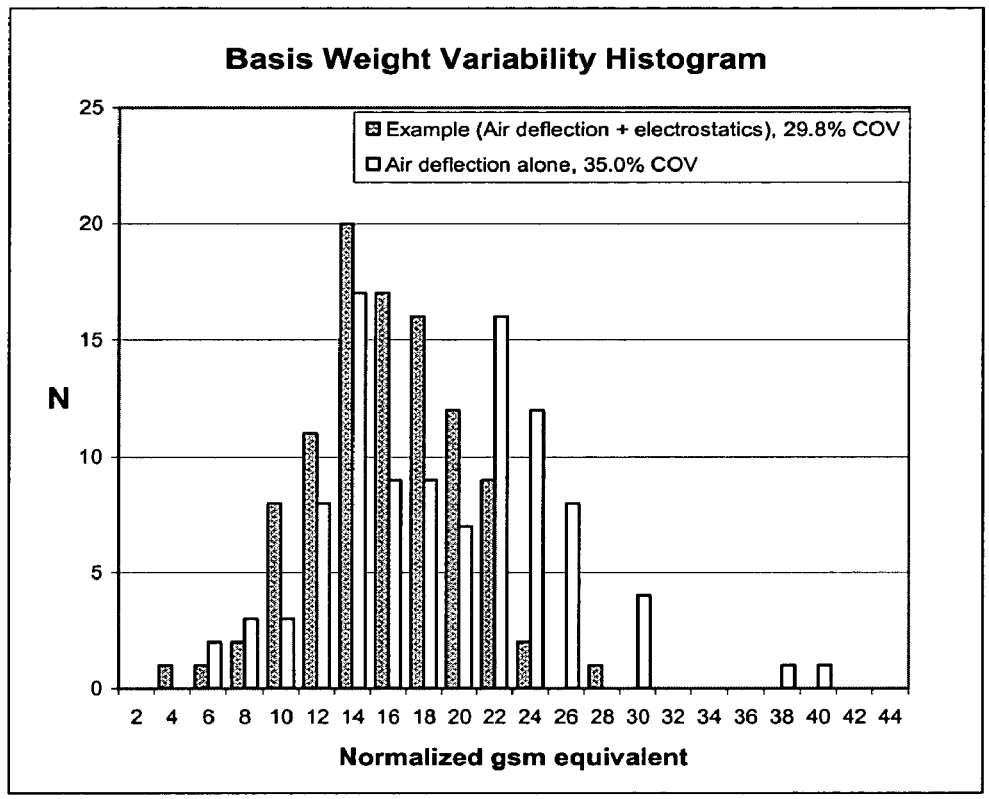
FIG. 5 is a bar graph illustrating basis weight variability in nonwoven webs.

To assess the uniformity of basis weight, one hundred circles of 2.54 centimeter diameter were randomly cut from a 1 square meter sample of spunbond fabric. The weight of each circle was measured and then normalized on a per unit area basis. The results of the test can be seen in FIG. 5, which is a histogram bar chart the number of circles "N" measured at each normalized weight for each of the two materials. The basis weight uniformity of the two materials is compared as a calculated coefficient of variation or "COV". Percent COV is calculated as the standard deviation of the test results divided by the average of the test results, and multiplied by 100 so as to be expressed as a percent. The COV for the Example spunbond material was about 5% better than the COV for the comparative spunbond material made with air deflection alone (29.8% for the Example versus 35.0% for the comparative). It was also noted upon visual inspection of the materials that the visual appearance of the formation of the Example spunbond material was superior compared to the spunbond material made using the air deflectors alone, which material exhibited a more mottled or splotchy appearance indicated by heavy and light spots in the material.

Figure 6:
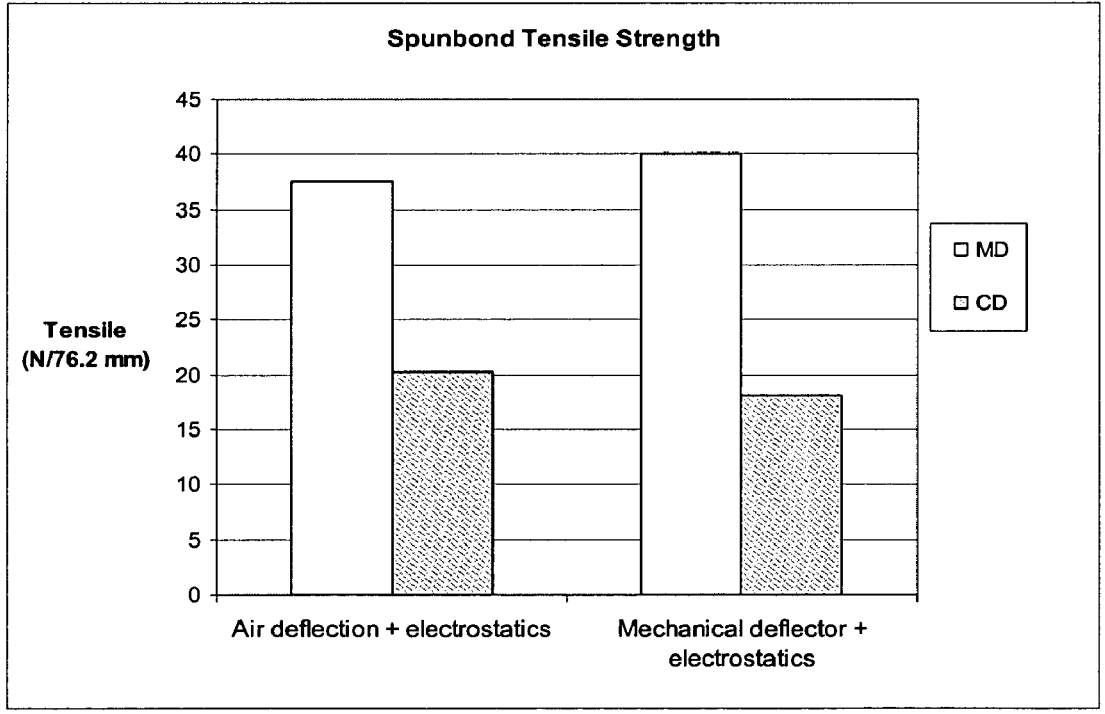
FIG. 6 is a bar graph illustrating tensile strengths of nonwoven webs.

Tensile strength testing was performed using a Sintech 2/S tensile tester available from the SinTech Corporation (Carey, N.C.) in accordance with ASTM-D-5035-90, except that 3 inch (76.2 mm) cut strip samples were used instead of the one inch (25.4 mm) or two inch (50.8 mm) samples specified in procedure D-5035-90. Ten samples were tested for tensile strength in each of the CD and MD directions and the results were averaged for each material and normalized to a 0.5 osy (17 gsm) unit weight. Results from these tests are shown graphically in FIG. 6. As can be seen from FIG. 6, the CD tensile strength of the Example material was directionally improved when compared to the comparative spunbond made using the electrostatics and angled tooth mechanical deflection. For the Example material, the average CD tensile strength was 20.23 N/76.2 mm, which is over 12% greater than the 18.05 N/76.2 mm result for the CD tensile strength of the comparative spunbond made using the electrostatics and angled tooth mechanical deflection.

Numerous other patents have been referred to in the specification and to the extent there is any conflict or discrepancy between the teachings incorporated by reference and that of the present specification, the present specification shall control. Additionally, while the invention has been described in detail with respect to specific embodiments thereof, it will be apparent to those skilled in the art that various alterations, modifications and/or other changes may be made without departing from the spirit and scope of the present invention. It is therefore intended that all such modifications, alterations and other changes be encompassed by the claims.

The invention claimed is:

1. A method of making a nonwoven web comprising:
  a) providing a source of fibers;
  b) subjecting the fibers to an electrostatic charge;
  c) deflecting the fibers with a non-contacting deflecting device, wherein said non-contact deflecting device comprises an air jet deflector providing discrete jets of air at a downward angle with respect to a horizontal plane and a sideward angle from a machine direction (MD) of the nonwoven web; and
  d) collecting the fibers on a moving forming surface to form the nonwoven web.

2. The method of claim 1 wherein the fibers are substantially continuous fibers provided by melt spinning.

3. The method of claim 2 wherein the fibers are subjected to pneumatic drawing forces prior to being subjected to the electrostatic charge.

4. Presented) The method of claim 1 wherein the air jet deflector provides perturbed jets of air.

5. The method of claim 1 wherein the electrostatic charge is provided using a charged pin array.

6. The method of claim 5 wherein the air jet deflector is a target electrode for the charged pin array.

7. The method of claim 1 wherein the air jets are angled with respect to the machine direction at an angle of about 15 degrees to about 60 degrees.

8. The method of claim 1 wherein the air jets are angled downward with respect to the horizontal plane at an angle up to about 60 degrees.

9. An apparatus for forming a fibrous nonwoven web comprising:
  a) a source of fibers;
  b) a device for applying an electrostatic charge to the fibers;
  c) a non-contacting fiber deflecting device adapted to affect the fibers while the fibers are under the influence of the applied electrostatic charge, wherein said non-contact deflecting device comprises an air jet deflector for providing discrete jets of air at a downward angle with respect to a horizontal plane and a sideward angle from a machine direction (MD) of the nonwoven web; and
  d) a forming surface for collecting the fibers as a fibrous nonwoven web.

10. The apparatus of claim 9 wherein the source of fibers is a melt spinning device for producing continuous fibers and wherein the device for applying the electrostatic charge is a charged pin array, and the apparatus further including a fiber drawing unit applying pneumatic drawing forces to the continuous fibers.

11. The apparatus of claim 10 wherein the device for applying the electrostatic charge to the fibers is located to apply the electrostatic charge before the fibers enter the fiber drawing unit.

12. The apparatus of claim 10 wherein the device for applying the electrostatic charge to the fibers is located to apply the electrostatic charge to the fibers while the fibers are in the fiber drawing unit.

13. The apparatus of claim 10 wherein the device for applying the electrostatic charge to the fibers is located to apply the electrostatic charge to the fibers after the fibers exit the fiber drawing unit and before the fibers are collected on the forming surface.

14. The apparatus of claim 12 wherein the air jet deflector is located on the opposite side of the fibers from the device for applying the electrostatic charge, and wherein the air jet deflector is a target electrode.

15. The apparatus of claim 13 wherein the air jet deflector is located on the opposite side of the fibers from the device for applying the electrostatic charge, and wherein the air jet deflector is a target electrode.

16. The apparatus of claim 13 further comprising a second air jet deflector located on the opposite side of the fibers from the first air jet deflector.

17. The apparatus of claim 16 wherein the charged pin array is located upon one non-contacting deflection device.

* * * * *